United States Patent [19]

Deraedt et al.

[11] 4,424,218
[45] Jan. 3, 1984

[54] NOVEL 3 α-AMINO STEROIDS

[75] Inventors: Roger Deraedt, Pavillons-sous-Bois; Vesperto Torelli, Maisons-Alfort; Jean Vacher, Paris; Josette Benzoni, Livry-Gargan, all of France

[73] Assignee: Roussel Uclaf, Paris, France

[21] Appl. No.: 292,791

[22] Filed: Aug. 14, 1981

Related U.S. Application Data

[63] Continuation-in-part of Ser. No. 177,845, Aug. 14, 1980, abandoned.

[30] Foreign Application Priority Data

Aug. 17, 1979 [FR] France .................. 79 20840
Nov. 21, 1980 [FR] France .................. 80 24750

[51] Int. Cl.³ ............................................. A01N 45/00
[52] U.S. Cl. ................................ 424/238; 260/397.5; 260/397; 260/397.3; 260/397.4
[58] Field of Search ................... 260/397.5; 424/238

[56] References Cited

U.S. PATENT DOCUMENTS 3,424,747 1/1969 Schmitt et al. .............. 260/239.5
4,093,721 6/1978 Teutsch et al. .............. 260/397.45
4,232,015 11/1980 Phillipps et al. .............. 260/397.45

Primary Examiner—Elbert L. Roberts
Attorney, Agent, or Firm—Hammond & Littell, Weissenberger and Muserlian

[57] ABSTRACT

A 3-amino-steroid of the formula

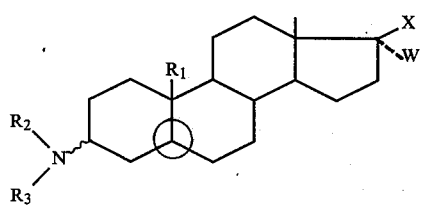

wherein W is selected from the group consisting of hydrogen and —OH and taken together with X is ethylidene, X is selected from the group consisting of ethyl,

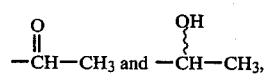

the wavy line indicates the substituent has the α- and β-position, $R_1$ is selected from the group consisting of hydrogen and —CH$_3$, $R_2$ is selected from the group consisting of hydrogen, alkyl of 1 to 5 carbon atoms and hydroxyalkyl of 2 to 5 carbon atoms, $R_3$ is selected from the group consisting of hydrogen, alkyl of 1 to 5 carbon atoms, hydroxyalkyl of 2 to 5 carbon atoms, acyl of organic acid of 2 to 8 carbon atoms, alkoxycarbonyl of 2 to 8 carbon atoms, acyl of an α-amino-carboxylic acid and a peptide of 2 to 3 α-amino-carboxylic acids and their non-toxic, pharmaceutically acceptable acid addition acids with the proviso that $R_2$ and $R_3$ are not both hydrogen and (i) when $R_1$ is methyl, W and $R_2$ are hydrogen and X is

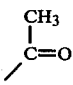

in the case $R_3$ is not methyl, acetyl or derived from an anminocarboxylic acid, (ii) when $R_1$ is —CH$_3$, W is hydrogen, $R_2$ is —CH$_3$ and X is

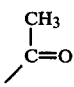

in the case $R_3$ is not methyl or acetyl, (iii) when $R_1$ is methyl, $R_2$ and W are hydrogen, X is

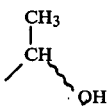

with the —OH having the (S) configuration and the amino group is in the α-position in the case $R_3$ is not methyl (iiii) $R_2$ and W are hydrogen, X is

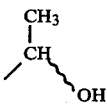

and the 3-amino is in the α-position in the case at least one of $R_1$, $R_2$ and $R_3$ is not methyl and (iiiii) $R_2$ and W are hydrogen, $R_1$ is methyl, X is

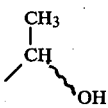

with the —OH having the (R) configuration and the 3-amino is in the α-position in the case $R_3$ is not ethoxycarbonyl capable of stimulating the defenses of an organism, especially by potentializing the production of IgE (immunoglobulins E) and their preparation.

10 Claims, No Drawings

NOVEL 3 α-AMINO STEROIDS

PRIOR APPLICATION

This application is a continuation-in-part of commonly assigned, copending patent application Ser. No. 177,845 filed Aug. 14, 1980, now abandoned.

STATE OF THE ART

Related prior art are U.S. Pat. No. 3,196,169 and Bull. Soc. Chim. France, Vol. No. 10 (1967) and C. R. Acad Sciences Paris, Vol. 260 (Jan. 11, 1965).

OBJECTS OF THE INVENTION

It is an object of the invention to provide the novel compounds of formula I and their non-toxic, pharmaceutically acceptable acid addition salts and a process for their preparation.

It is another object of the invention to provide novel compositions and a novel method for the treatment of autoimmuno maladies.

These and other objects and advantages of the invention will become obvious from the following detailed description.

THE INVENTION

The novel compounds of the invention are selected from the group consisting of 3-amino-steroids of the formula

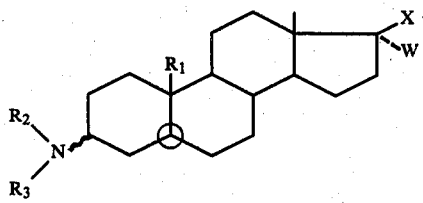

wherein W is selected from the group consisting of hydrogen and —OH and taken together with X is ethylidene, X is selected from the group consisting of ethyl,

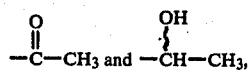

the wavy line indicates the substituent has the α- or β-position, $R_1$ is selected from the group consisting of hydrogen and —CH$_3$, $R_2$ is selected from the group consisting of hydrogen, alkyl of 1 to 5 carbon atoms and hydroxyalkyl of 2 to 5 carbon atoms, $R_3$ is selected from the group consisting of hydrogen, alkyl of 1 to 5 carbon atoms, hydroxyalkyl of 2 to 5 carbon atoms, acyl of an organic acid of 2 to 8 carbon atoms, alkoxycarbonyl of 2 to 8 carbon atoms, acyl of an α-amino-carboxylic acid and a peptide of 2 to 3 α-amino-carboxylic acids and their non-toxic, pharmaceutically acceptable acid addition salts with the proviso that $R_2$ and $R_3$ are not both hydrogen and (i) when $R_1$ is methyl, W and $R_2$ are hydrogen and X is

in the case $R_3$ is not methyl, acetyl or derived from an aminocarboxylic acid, (ii) when $R_1$ is —CH$_3$, W is hydrogen, $R_2$ is —CH$_3$ and X is

in the case $R_3$ is not methyl or acetyl, (iii) when $R_1$ is methyl, $R_2$ and W are hydrogen, X is

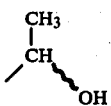

with the —OH having the (S) configuration and the amino group is in the α-position in the case $R_3$ is not methyl (iiii) $R_2$ and W are hydrogen, X is

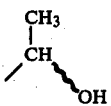

and the 3-amino is in the α-position in the case at least one of $R_1$, $R_2$ and $R_3$ is not methyl and (iiiii) $R_2$ and W are hydrogen, $R_1$ is methyl, X is

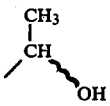

with the —OH having the (R) configuration and the 3-amino is in the α-position in the case $R_3$ is not ethoxycarbonyl.

In the compounds of formula I, examples of alkyl of 1 to 5 carbon atoms are methyl, ethyl, propyl, isopropyl, butyl, isobutyl and pentyl and examples of hydroxyalkyl of 2 to 5 carbon atoms are hydroxyethyl and hydroxypropyl. Examples of acyl of an organic carboxylic acid of 2 to 8 carbon atom are acetyl, propionyl, n-butyryl, isobutyryl, benzoyl and nicotinyl and examples of alkoxycarbonyl are methoxycarbonyl, ethoxycarbonyl and propoxycarbonyl. Derivatives of amino carboxylic acids are selected from the group consisting of Ala, Val, Ival, Leu, Ile, Asp, Asn, Gln, Ser, Thr, Cys, Met, Lys, Argl, Phe, Tyr, Trp, His, Pro, Nva, Nle, Hyp and Orn in their D or L form as well as Sar and Gly. Examples of a peptide of 2 to 3 α-amino acids are made up of the above α-amino acids.

By convection, the symbols of α-amino carboxylic acids represents acids of either the D or L configuration. For example, Ala signifies Alanine in either the D form or the L form. Except for contrary convention, the nomenclature used in the application is IUPAC nomenclature by the rules published in Biochem. J., Vol. 126 (1972), p. 773–780.

Examples of suitable acids for the preparation of the non-toxic, pharmaceutically acceptable acid addition salts are inorganic acids such as sulfuric acid, hydrochloric acid, hydrobromic acid, nitric acid, hydroiodic acid and phosphoric acid and organic acids such as formic acid, acetic acid, benzoic acid, maleic acid, fumaric acid, succinic acid, tartaric acid, citric acid, oxalic acid, glyoxylic acid, aspartic acid, alkane sulfonic acids such as methane sulfonic acid and arylsulfonic acids such as benzene sulfonic acid.

Among the preferred compounds of the invention are those wherein X is

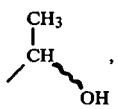

those wherein $R_2$ is hydrogen or methyl and their non-toxic-pharmaceutically acceptable acid addition salts. Especially preferred are (20S) 3α-[amino-acetylamino]-6=-pregnane-20-ol, 2-amino-N[(20S) 5α-pregnane-20-ol-3α-yl]-propanamide, (2S) 2-amino-N-[(20S) 5α-pregnane-20-ol-3α-yl]-1H-indol-3-propanamide, 2-amino-N-[(20S) 19-nor-5α-pregnane-20-ol-3α-yl]-acetamide, 2-amino-N-[(20S) 5α-pregnane-20-ol-3α-yl]-N-methyl-acetamide and their non-toxic, pharmaceutically acceptable acid addition salts.

The novel process of the invention for the preparation of a compound of formula I comprises reacting a amine of the formula

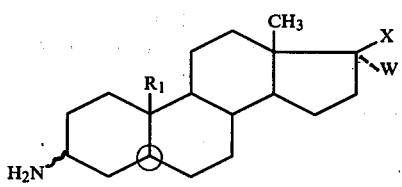

wherein X, W, $R_1$ and the wavy line have the above definition with either (A) a halide of the formula

    III wherein Hal is chlorine, bromine or iodine and $R_3'$ is selected from the group consisting of acyl of an organic carboxylic acid of 2 to 8 carbon atoms and alkoxy carbonyl of 2 to 8 carbon atoms to obtain the corresponding compound of formula I wherein $R_2$ is hydrogen and $R_3$ is $R_3'$ which may be salified, if desired or (B) with an α-amino acid or a peptide of 2 to 3 α-amino acids with the amino group protected by an easily cleavable group, especially by acid hydrolysis and then removing the protective group to obtain a compound of formula I wherein $R_2$ is hydrogen and $R_3$ is an α-amino acid derivative or a derivative of a peptide of 2 to 3 amino acids which, if desired, may be salified or (C) with an alkyl halide of 1 to 5 carbon atoms or hydroxyalkyl halide of 2 to 5 carbon atoms and the halogen is chlorine, bromine or iodine to obtain the corresponding compound of formula I wherein $R_2$ and $R_3$ are selected from the group consisting of hydrogen, alkyl of 1 to 5 carbon atoms and hydroxy alkyl of 2 to 5 carbon atoms which, if desired, may be salified and in the case when $R_3$ is hydrogen, is reacted with a halide of the formula

    IV wherein $R_3''$ is selected from the group consisting of alkyl of 1 to 5 carbon atoms, hydroxyalkyl of 2 to 5 carbon atoms, acyl of an organic carboxylic acid of 2 to 8 carbon atoms and alkoxycarbonyl of 2 to 8 carbon atoms and Hal is chlorine, bromine or iodine to obtain the corresponding compound of formula I wherein $R_3$ is $R_3''$ and $R_2$ is selected from the group consisting of alkyl of 1 to 5 carbon atoms and hydroxyalkyl of 2 to 5 carbon atoms which, if desired, may be salified or when $R_3$ is hydrogen, the compound of formula I may be reacted with an α-amino acid or a peptide of 2 to 3 α-amino acids with the amino groups protected by an easily cleavable group, especially by acid hydrolysis, and then removing the protective group to obtain the corresponding compound of formula I wherein $R_2$ is alkyl of 1 to 5 carbon atoms or hydroxyalkyl of 2 to 5 carbon atoms and $R_3'$ is derivative of an α-amino acid or a peptide of 2 to 3 amino acids which, if desired, may be salified.

In a preferred mode of the process of the invention, the reaction of the amine of formula II with the halide of formula III is effected in the presence of an acid binding agent such as alkali metal hydroxides, alkali metal carbonates such as potassium carbonate, alkali metal bicarbonates, alkali metal acetates, alkali metal carbonates, tertiary amines such as pyridine or trialkylamines or alkali metal alcoholates such as sodium ethylate. The said reaction is preferably in a solvent or an inert suspension such as lower aliphatic ketones, dioxane, dimethylformamide, benzene or toluene. In the case of acylation, one can use also the free acid or a functional derivative thereof such as the acid anhydride.

Another method of attaching the $R_3'$ group consists of transforming from the first the amino group of the compound of formula II to obtain the corresponding alkaline compound by reacting the latter in an inert organic solvent such as dioxane, dimethylformamide, benzene or toluene with an alkali metal, alkali metal hydride or alkali metal amide, especially sodium or sodium derivatives, at a temperature from 0° to 150° C. and reacting the product with an acid acylating agent such as the acid chloride or acid anhydride. In this case or when the free acid is used, it is necessary to activate the reaction by the presence of condensation agents such as carbodiimide or dialkylamides of sulfurous acid.

In the reaction of an amine of formula II or a compound of formula I wherein $R_3$ is hydrogen and $R_2$ is alkyl of 1 to 5 carbon atoms or hydroxyalkyl of 2 to 5 carbon atoms with an α-amino acid or a peptide of 2 to 3 α-amino acids, the amino group is protected by an easily cleavable group, the presence of a condensation agent is used to activate the acid group of the amino acid. Examples of suitable condensation agents are carbodiimides of the formula

A—N═C═N—B wherein A and B are alkyl of 1 to 8 carbon atoms optionally containing a dialkylamino or cycloalkyl such as dicyclohexylcarbodiimide or preferably 1-ethyl-3-(3-dimethylaminopropyl)carbodiimide.

Also useful is an alkyl chloroformate such as methyl chloroformate, ethyl chloroformate or isobutyl chloroformate or an alkyl pyrophosphite such as ethylpyrophosphite. The easily cleavable protective group may be carbobenzyloxy or preferably carbotert.-butoxy.

The easily cleavable protective group may be removed by treatment with an acid cleaving agent such as hydrochloric acid such as hydrogen chloride in solution in an alkanol or by bubbling gaseous hydrogen chloride into nitromethane. Also useful are p-toluene sulfonic acid, formic acid or trifluoroacetic acid or hydrogen in the presence of palladium.

The reaction of the amine of formula II with an alkyl halide or hydroxyalkyl halide is effected in the presence of the above acid fixation agents and organic solvents used in the case of the reaction with the halide of formula III. The hydroxy group of the hydroxyalkyl is preferably blocked by an easily cleavable protective group such as by acid hydrolysis. A preferred protective group is tetrahydropyranyl which can be cleaved under the same conditions as the amino protective group.

The reaction of the compound of formula I wherein $R_3$ is hydrogen and $R_2$ is alkyl of 1 to 5 carbon atoms or hydroxyalkyl of 2 to 5 carbon atoms with a halide of formula IV is effected under the same conditions as the reaction of the amine of formula II and the halide of formula III.

To prepare the N-alkyl derivatives of formula I, it is interesting in certain cases to operate in a particular fashion. For example, to prepare N-monoethyl compound of formula I, the corresponding N-acetyl derivative is formed and then reduced. To prepare the N,N-diethyl derivative of formula I, the said operation is repeated. To prepare the N-mono isopropyl or N,N-diisopropyl compound of formula I, the compound of formula II is reacted with acetone in the presence of a reducing agent such as sodium cyanoborohydride.

The compounds of formula I except those wherein $R_3$ is acyl or acyloxy have a basic character and the acid addition salts thereof may be formed by reacting about stoichiometric proportions of the acid and the compound of formula I and the bases need not be isolated.

The starting compounds of formula II which are not known may be prepared by reacting a compound of the formula

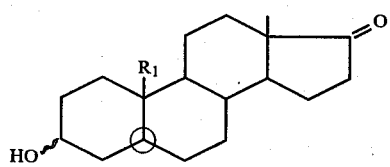

V wherein $R_1$ and the wavy line have the above meaning with an excess of ethyl triphenylphosphonium bromide and potassium tert.-butylate to obtain a compound of the formula

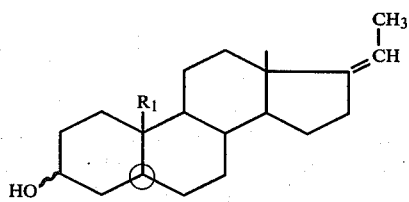

VI forming its azide by preparing its tosylate then reacting the latter with sodium azide, or by reacting compound VI with diphenyl azidophosphate or ethyl azodicarboxylate to obtain a compound of the formula

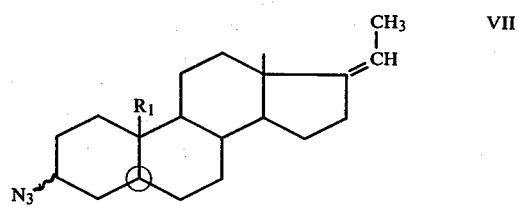

VII and reducing the latter such as by reaction with lithium aluminium hydride to obtain an amine of the formula

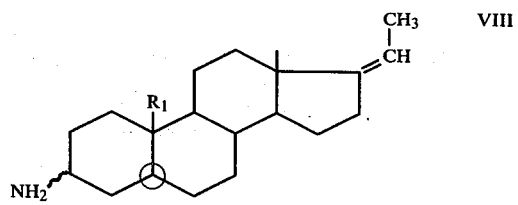

VIII and either reacting the latter with a diborane to obtain a compound of the formula

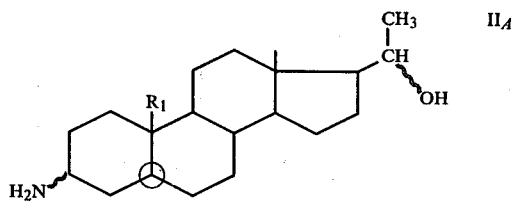

II$_A$ which may be recovered or oxidized such as with chromic acid to obtain a compound of the formula

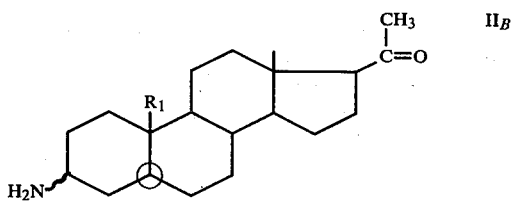

II$_B$ which may be salified or the compound of formula VII may be subjected to a cis dihydroxylation, for example by reaction with trimethoxyamine, preferably after protection of the amino group with an easily hydrolyzable group such as trifluoroacetyl to obtain a compound of the formula

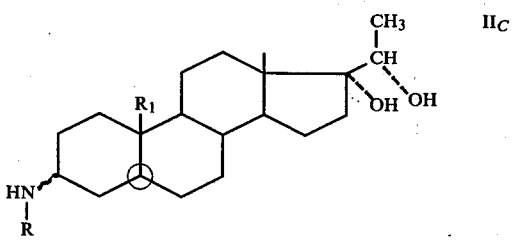

II$_C$ wherein R is hydrogen or a protective group and when R is hydrogen, recovering the product and when R is a protective group, subjecting the compound to a cleavage agent to remove the group such as an alkaline hydrolysis in the case of trifluoroacetyl and recovering the product or oxidizing the compound of formula II$_C$ such as with chromic acid to obtain a compound of the formula

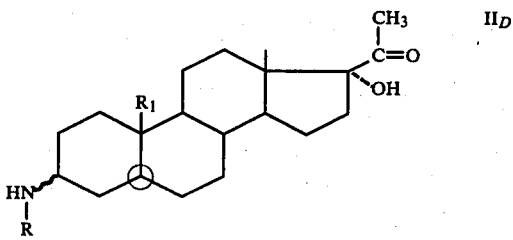

and when R is hydrogen, recovering the product and when R is a protective group treating the compound with a cleavage agent and recovering the free amine or reducing the latter with sodium borohydride, for example, to obtain a compound of the formula

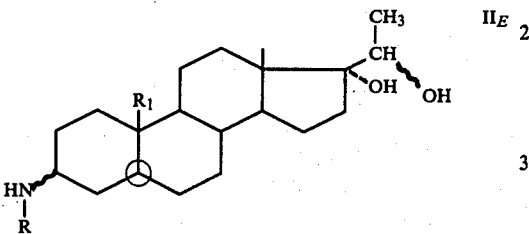

which may be recovered when R is hydrogen or treated with a cleavage agent when R is a protective group and then recovering the free amine.

The novel compositions of the invention for the treatment of autoimmuno maladies are comprised of at least one compound selected from the group consisting of a compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions.

Examples of suitable excipients are talc, arabic gum, lactose, starch, magnesium stearate, cacao butter, aqueous or non-aqueous vehicles, fatty bodies of vegetable or animal origin, paraffinic derivatives, glycols, diverse wetting agents, emulsifiers or dispersants and preservatives.

The compositions are useful for the treatment of autoimmuno maladies resulting from a deficiency of certain lymphocytes such as maladies of conjunctive tissue which are non-specific of an organ such as rhumatoidal arthritis or systemic erythematous lupus or specific maladies of an organ such as thyroiditis, pemphygus or hemolytic anaemia. The compositions are also useful as adjuvant treatment of anticancer chemotherapy and antibiotherapy.

Among the preferred compositions of the invention are those wherein X is

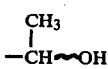

and those wherein R$_2$ is hydrogen or methyl and their non-toxic, pharmaceutically acceptable acid addition salts. Especially preferred are (20s) 3α-[aminoacetylamino]-5α-pregnane-20-ol, 2-amino-N-[(20S) 5α-pregnane-20-ol-3α-yl]-propanamide, (2S) 2-amino-N-[(20S) 5α-pregnane-20-ol-3α-yl]-1H-indol-3-propanamide, 2-amino-N-[(20S) 19-nor-5α-pregnane-20-ol-3α-yl]-acetamide, 2-amino-N-[(20S) 5α-pregnane-20-ol-3α-yl]-N-methyl-acetamide and their non-toxic, pharmaceutically acceptable acid addition salts.

The novel method of the invention of treating autoimmuno maladies in warm-blooded animals, including humans, comprises administering to warm-blooded animals an amount sufficient to treat autoimmuno maladies of at least one compound selected from the group consisting of a compound of formula I and their non-toxic, pharmaceutically acceptable acid addition salts. The compounds may be administered orally, rectally or parenterally. The usual daily dose is 0,1 to 10 mg/kg depending on the affection being treated, the patient and the method of administration.

In the following examples there are described several preferred embodiments to illustrate the invention. However, it should be understood that the invention is not intended to be limited to the specific embodiments.

EXAMPLE 1

(20S) 3α-[(aminoacetyl)-amino]-5α-pregnane-20-ol hydrochloride

STEP A: (20S) 3α-[benzyloxycarbonylaminoacetyl)-amino]-5α-pregnane-20-ol 3.9 g of 1-ethyl-3-(3-dimethylaminopropyl)-carbodiimide hydrochloride were added under nitrogen to a stirred solution of 5.2 g of (20S) 3α-amino-5α-pregnane-20-ol, 5.2 g of N-carbobenzyloxyglycine, 15 ml of pyridine and 150 ml of chloroform in an ice bath and after one hour, another 310 mg of 1-ethyl-3-(3-dimethylaminopropyl)-carbodiimide hydrochloride were added thereto with stirring. The mixture was stirred for 30 minutes in the ice bath and was then diluted with aqueous sodium bicarbonate solution. The mixture was filtered and the insoluble phase was washed with aqueous sodium bicarbonate solution, with water, with N hydrochloric acid and with water and dried at 50° C. to obtain 5.1 g of insolubles. The chloroform phase was recovered from the filtrate and was washed with water, with N hydrochloric acid, with water, dried and evaporated to dryness. The 4.6 g of semicrystalline residue and the 5.1 g of insolubles were empasted at reflux with 25 ml of methanol and the mixture was iced and vacuum filtered. The product was washed with methanol and dried at 50° C. to obtain 7.05 g of (20S) 3α-[(benzyloxycarbonylaminoacetyl)-amino]-5α-pregnane-20-ol melting at 250°-252° C. which was used as is for the next step. After crystallization of a sample from acetic acid, the product melted at 254° C.

STEP B: (20S) 3α-[(aminoacetyl)-amino]-5α-pregnane-20-ol-hydrochloride 7 g of the product of Step A were dissolved in 150 ml of hot acetic acid and the mixture was stirred while nitrogen was bubbled therethrough. The mixture was cooled to 45° C. and 700 mg of 10% palladized carbon were added thereto. The nitrogen bubbling was replaced by slow bubbling of hydrogen and after about one hour, nitrogen replaced the hydrogen stream for 15 minutes. The mixture was filtered to remove the catalyst and the filter was rinsed with acetic acid. The filtrate was evaporated to dryness and the crystalline residue was dissolved in 50 ml of methanol. 4 ml of 5.5 N hydrogen chloride in ethanol were added to the solution and a precipitate formed. The suspension was diluted with 50 ml of absolute ethanol and was concentrated to half its volume. The mixture stood overnight at 5° C. and was vacuum filtered. The product was washed with ethanol and was dried to obtain 4.43 g of (20S) 3α-[(aminoacetyl)-amino]-5α-pregnane-20-ol hydrochloride which after crystallization from 80% ethanol melted at 271° C. and had a specific rotation of $[\alpha]_D^{20} = +19.5° \pm 1°$ (c=1% in pyridine containing 10% water). Addition of 0.5 ml of a 5.5 N hydrogen chloride in ethanol to the filtrate and concentration of the mixture to a small volume yielded another 0.35 g of the desired product.

STEP C: (20S) 3α-[(aminoacetyl)-amino-]-5α-pregnane-20-ol

The raw product of Step B was dissolved in hot water and then an excess of 2 N sodium hydroxide solution was added to make the mixture alkaline. The mixture was vacuum filtered and the recovered product was washed with water, dried and crystallized from methanol to obtain (20S) 3α-[(aminoacetyl)-amino]-5α-pregnane-20-ol melting at 269° C. and having a specific rotation of $[\alpha]_D^{20} = +25° \pm 1°$ (c=1% in pyridine containing 10% of water).

EXAMPLE 2
(2S) 2-amino-N-[(20S)-5α-pregnan-20-ol-3α-yl]-propanamide

STEP A: 2-[1,1-dimethylethoxycarbonylamino]-N-[(20S)-5α-pregnan-20-ol-3α-yl]-propanamide 1.14 g of 1-ethyl-3-(3-dimethylaminopropyl)-carbodiimide hydrochloride were added with stirring under an inert atmosphere at 0° to 5° C. to a solution of 1.92 g of (20S) 3α-amino-5α-pregnan-20-ol, 2.27 g of tert.-butyloxycarbonyl-L-alaine (BOC-L-Alanine), 60 ml of chloroform and 12 ml of pyridine and the mixture was stirred for 75 minutes after which another 1.15 g of 1-ethyl-3-(3-dimethylaminopropyl)-carbodiimide hydrochloride was added thereto. The mixture was stirred at 0° to 5° C. for 50 minutes and was evaporated to dryness. The residue was taken up in aqueous sodium bicarbonate solution and the solution was extracted with ethyl acetate. The organic phase was washed with aqueous saturated sodium chloride and then with aqueous N hydrochloric acid and then with aqueous saturated sodium chloride solution, dried and evaporated to dryness. The residue was crystallized from isopropyl ether and was vacuum filtered. The product was rinsed with isopropyl ether and dried at 60° C. under reduced pressure to obtain 2-[1,1-dimethylethoxycarbonylamino]-N-[(20S)-5α-pregnan-20-ol-3α-yl]-propanamide melting at 171° C.

STEP B: (2S) 2-amino-N-[(20S)-5α-pregnan-20-ol-3α-yl]-propanamide

Gaseous hydrogen chloride was bubbled through a suspension of 1.55 g of the product of Step A in 100 ml of nitromethane under an inert atmosphere for 10 minutes and the mixture was stirred at 20°-25° C. for 35 minutes. Excess hydrogen chloride was removed and the mixture was vacuum filtered. The product was rinsed with ether and dried at 60° C. under reduced pressure and was crystallized from methanol to obtain 990 mg of (2S) 2-amino-N-[(20S)-5α-pregnan-20-ol-3α-yl]-propanamide hydrochloride melting at 220° C.

4 ml of 2 N sodium hydroxide were added to a solution of 1.74 g of said hydrochloride in 100 ml of tetrahydrofuran containing 30% water and the mixture was evaporated to dryness. The residue was taken up in 100 ml of chloroform and the solution was washed with water, dried and evaporated to dryness. The residue was crystallized from ethyl acetate to obtain 1.27 g of (2S) 2-amino-N-[(20S)-5α-pregnan-20-ol-3α-yl]-propanamide melting at 224° C.

In a variation, 40 ml of 3.5 N ethanolic hydrochloric acid were added under an inert atmosphere to a solution of 2.7 g of the product of Step A in 10 ml of ethanol and the mixture was stirred for 8 hours and was then evaporated to dryness. The residue was taken up in ethyl acetate and the solution was iced and vacuum filtered. The product was washed with ethyl acetate, was dried at 60° C. under reduced pressure and was crystallized from methanol to obtain 2.2 g of (2S) 2-amino-N-[(20S)-5α-pregnan-20-ol-3α-yl]-propanamide hydrochloride melting at ≃220° C.

EXAMPLES 3 TO 8

Using the procedure of Example 2, the amine and steroid of Table I were reacted to obtain the corresponding amino-steroid.

| Example | Variant | Amino Acid | R₃ | Melting Point °C. |
|---|---|---|---|---|
| 3 | 1* | BOC—L-Glutamic Acid | 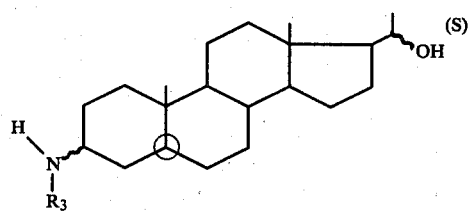 | 220 (hydrochloride) |

-continued

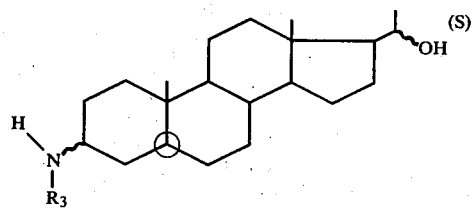

| Example | Variant | Amino Acid | R₃ | Melting Point °C. |
|---|---|---|---|---|
| 4 | 1 | BOC—L-Serine | O=C(—)—CH(NH₂)—CH₂OH (S) | 210 (hydrochloride) |
| 5 | 1 | BOC—L-Phenylalanine | O=C(—)—CH(NH₂)—CH₂—C₆H₅ (S) | 240 (hydrochloride) |
| 6 | 1 | BOC—L-Tryptophan | O=C(—)—CH(NH₂)—CH₂—(indolyl) (S) | 135° C. (base) |
| 7 | 2 | BOC—L-Proline | O=C(—)—CH—(pyrrolidinyl) (S) | 275 (hydrochloride) |
| 8 | CF₃COOH | BOC—Glycyl Glycine | O=C(—)—CH₂—NH—CO—CH₂—NH₂ | 240 hydrochloride 200 then 252° C. base |

*The second acid group of L-glutamic acid was blocked in benzyl ester form which was removed by catalytic hydrogenation in acetic acid in the presence of palladium before BOC cleavage.

EXAMPLE 9

N-[(20S)5α-pregnan-20-ol-3α-yl]-3-pyridinecarboxamide 582 mg of 1-ethyl-3-(3-dimethylaminopropyl)-carbodiimide hydrochloride were added under an inert atmosphere to a solution of 960 mg of (20S) 3α-amino-5α-pregnane-20-ol, 813 mg of nicotinic acid, 30 ml of chloroform and 6 ml of pyridine and after 3½ hours, another 291 mg of 1-ethyl-3-(3-dimethylaminopropyl)-carbodiimide hydrochloride were added to the mixture. The mixture was stirred for 16 hours and was evaporated to dryness. The residue was taken up in 30 ml of water and the solution was iced and vacuum filtered. The product was washed with water, dried at 80° C. under reduced pressure and was crystallized from methanol to obtain 920 mg of N-[(20S) 5α-pregnan-20-ol-3α-yl]-3-pyridinecarboxamide melting at 258° C. and having a specific rotation of $[\alpha]_D^{20} = +14.5° \pm 1°$ (c=1% in pyridine).

EXAMPLE 10

2-amino-N-[(20S) 5α-pregnane-17α,20-diol-3α-yl]-acetamide hydrochloride

STEP A: (Z)Δ¹⁷⁽²⁰⁾-5α-pregnene-3β-ol

A mixture of 59.4 g of triphenylethylphosphonium bromide, 16.1 g of potassium tert.-butylate and 160 ml of tetrahydrofuran was stirred for 30 minutes and after the addition of 23.2 g of epiandrosterone, the mixture was stirred for 15 hours and was poured into iced water. The mixture was extracted with ethyl acetate and the organic phase was washed with water, dried and evaporated to dryness. The residue was chromatographed over silica gel and was eluted with a 7-3 cyclohexane-ethyl acetate mixture. The eluant was evaporated to dryness and the residue was taken up in methanol. The iced solution was vacuum filtered and the product was dried in air to obtain 23.1 g of (Z) Δ¹⁷⁽²⁰⁾-5α-pregnene-3α-ol melting at 160° C.

STEP B: (Z) 3α-azido-Δ¹⁷⁽²⁰⁾-5α-pregnene 1.92 g of ethyl azodicarboxylate and 3.02 g of diphenyl azidophosphate were added to a solution of 1.66 g of the product of Step A in 30 ml of benzene and 5 ml of tetrahydrofuran and the mixture was stirred in an ice bath while adding thereto over 20 minutes a solution of triphenylphosphine in 30 ml of benzene. The mixture was stirred at 10° C. for 40 minutes and was washed with water, dried and evaporated to dryness. The residue was chromatographed over silica gel and was eluted with heptane and then with a 1-1 heptane-acetone mixture to obtain after distillation 1.67 g of (Z) 3α-azido-$\Delta^{17(20)}$-5α-pregnene in thhe form of crystals melting at 106° C. and at 114° C. after crystallization from methanol.

STEP C: (Z) 3α-amino-$\Delta^{17(20)}$-5α-pregnene hydrochloride 14.5 g of the product of Step B were dissolved at 25°-27° C. in 290 ml of tetrahydrofuran and then 800 mg of lithium aluminum hydride were added to the mixture in an ice bath over one hour. The mixture was stirred for one hour and methanol was added to remove excess hydride. The mixture was filtered and the filtrate was washed with water, dried and evaporated to dryness to obtain 13.1 g of (Z) 3α-amino-$\Delta^{17(20)}$-5α-pregnene in the form of crystals melting at ≃90° C. The said product was dissolved in 150 ml of ethyl acetate and 30 ml of methylene chloride and 27 ml of 1.7 N hydrogen chloride in ethyl acetate were added thereto. The mixture was vacuum filtered and the product was washed and dried under reduced pressure to obtain 13.2 g of (Z) 3α-amino-$\Delta^{17(20)}$-5α-pregnene hydrochloride in the form of crystals melting at >300° C. and having a specific rotation of $[\alpha]_D^{20} = +38.5° \pm 1.5°$ (c=1% in pyridine containing 10% water).

STEP D: N-[(Z)$\Delta^{17(20)}$-5α-pregnene-3α-yl]-trifluoroacetamide 16.5 ml of trifluoroacetic acid anhydride were added over 5 minutes under an inert atmosphere at 5° C. to a suspension of 16.5 g of the product of Step C, 165 ml of methylene chloride and 16.5 ml of pyridine and the mixture was stirred at room temperature for 15 minutes and was evaporated to dryness under reduced pressure. 200 ml of water were added to the residue and the mixture was vacuum filtered. The product was washed with water and dried under reduced pressure to obtain 18.1 g of N-[(Z)$\Delta^{17(20)}$-5α-pregnene-3α-yl]-trifluoroacetamide in the form of crystals melting at 204° C.

STEP E: N-[(20S) 5α-pregnene-17α,20-diol-3α-yl]-trifluoroacetamide 9 g of the N-oxide of trimethylamine dihydrate and a solution of 360 mg of osmium tetraoxide in 71 ml of methyl ethyl ketone were added under an inert atmosphere to a solution of 18.1 g of the product of Step D in 100 ml of methyl ethyl ketone and the mixture was refluxed for 2 hours and then allowed to cool. 200 ml of a solution of 10% sodium thiosulfate in water were added to the mixture which was stirred at room temperature for 30 minutes. The decanted organic phase was washed with water, dried over magnesium sulfate, filtered and evaporated to dryness under reduced pressure. The oil residue was chromatographed over silica gel and was eluted with a 7-3 benzene-ethyl acetate mixture to obtain 14 g of N-[(20S)5α-pregnene-17α,20-diol-3α-yl]-trifluoroacetamide melting at 172° C., then 192° C.

STEP F: (20S) 3α-amino-5α-pregnane-17α,20-diol 8 ml of sodium hydroxide solution were added under an inert atmosphere to a solution of 4 g of the product of Step E in 20 ml of methanol and the mixture was stirred for 90 minutes. 50 ml of water were added to the mixture which was then stirred for 10 minutes and vacuum filtered. The product was washed and dried at 40° C. under reduced pressure to obtain 3 g of (20S) 3α-amino-5α-pregnene-17α,20-diol melting a 210° C.

STEP G: 2-amino-N-[(20S) 5α-pregnane-17α,20-diol-3α-yl]-acetamide hydrochloride Using the procedure of the variant of Example 2, the product of Step F and BOC-glycine were reacted to obtain 2-amino-N-[(20S) 5α-pregnane-17α,20-diol-3α-yl]-acetamide hydrochloride melting at ≃200° C. and having a specific rotation of $[\alpha]_D^{20} = +4° \pm 1°$ (c=1.5% in 95% ethanol).

EXAMPLE 11

2-amino-N-[(20S) 19-nor-5α-pregnane-20-ol-3α-yl]-acetamide hydrochloride

STEP A: (20S) 3α-amino-19-nor-5α-pregnane-20-ol

Using the procedure of Steps A to C of Example 10, 19-nor-epiandrosterone was reacted to obtain (Z) 3α-amino-19-nor-$\Delta^{17(20)}$-5α-pregnene. A solution of 0.5 ml of boron trifluoride etherate in 2.5 ml of tetrahydrofuran was added dropwise at 5° C. under nitrogen to a suspension of 156 mg of sodium borohydride in 5 ml of tetrahydrofuran and the mixture was stirred in an ice bath for one hour. A solution of 296 mg of (Z) 3α-amino-19-nor-$\Delta^{17(20)}$-5α-pregnene in 3 ml of tetrahydrofuran was added to the mixture which was stirred at room temperature for 90 minutes and then cooled in an ice bath. 2 ml of 6 N sodium hydroxide solution were slowly added to the mixture which was stirred at room temperature for 5 minutes. The decanted aqueous phase was extracted with tetrahydrofuran and the organic phase was washed and 4 ml of 5 N sodium hydroxide and 2 ml of water oxygenated to 110 volumes were added thereto. The mixture was stirred for 45 minutes and was extracted with ethyl acetate. The organic phase was washed, dried and evaporated to dryness under reduced pressure and the dry residue was taken up in 10 ml of methanol and 5 ml of N hydrochloric acid. The mixture was heated in a water bath at 50° C. for 30 minutes and was poured into aqueous saturated sodium bicarbonate solution. The mixture was extracted with methylene chloride and the organic phase was washed, dried and evaporated to dryness under reduced pressure to obtain 257 mg of (20S) 3α-amino-19-nor-5α-pregnane-20-ol in the form of crystals melting at ≃190° C.

STEP B: 2-amino-N-[(20S) 19-nor-5α-pregnane-20-ol-3α-yl)-acetamide hydrochloride Using the process of Example 1, BOC-glycine and the product of Step A were reacted to obtain 2-amino-N-[(20S) 19-nor-5α-pregnane-20-ol-3α-yl]-acetamide hydrochloride melting at ≃270° C. with sublimation and having a specific rotation of $[\alpha]_D^{20} = +39.5° \pm 1.5°$ (c=1% in methanol).

EXAMPLE 12

2-amino-N-[(5α-pregnane-17α-ol-20-one-3α-yl]-acetamide hydrochloride

The product of Step E of Example 10 was subjected to perchromic oxidation to obtain N-(5α-pregnane-17α-ol-20-one-3α-yl)-trifluoroacetamide melting at 178° C. and then 186° C. which was reacted according to Step F of Example 10 to obtain 3α-amino-5α-pregnane-17α-ol-20-one melting at 216° C. after crystallization from water.

Using the procedure of the variant of Example 2, the latter product and BOC-glycine were reacted to obtain 2-amino-N-[(5α-pregnane-17α-ol-20-one-3α-yl]-acetamide hydrochloride melting at >300° C. and having a specific rotation of $[\alpha]_D^{20} = +50° \pm 1°$ (c=1% in 95% ethanol).

EXAMPLE 13

2-amino-N-[(20R) 5α-pregnane-20-ol-3α-yl]-acetamide hydrochloride

Using the procedure of Example 2, BOC-glycine and (20R) 3α-amino-5α-pregnane-20-ol were reacted to obtain 2-amino-N-[(20R) 5α-pregnane-20-ol-3α-yl]-acetamide hydrochloride with a melting point of 210° C. and then 260° C. and having a specific rotation of $[\alpha]_D^{20} = +22° \pm 1°$ (c=0.8% in pyridine containing 10% water).

EXAMPLE 14

Ethyl N-[(20S)5α-pregnane-20-ol-3α-yl]-carbamate

A solution of 5 g of (20S) 3α-amino-5α-pregnane-20-ol in 500 ml of methylene chloride was added dropwise over 10 minutes under an inert atmosphere to a mixture of 15 ml of ethyl chloroformate and 45 ml of methylene chloride and the mixture was stirred for 30 minutes. 20 ml of N sodium hydroxide were added to the mixture which was stirred for 30 minutes. The mixture was decanted and extracted with methylene chloride. The organic phase was washed with water, dried, filtered and evaporated to dryness under reduced pressure. The residue was taken up in ether and the mixture was filtered to obtain 5.7 g of ethyl N-[(20S) 5α-pregnane-20-ol-3α-yl]-carbamate melting at ≃198° C. and having a specific rotation of $[\alpha]_D^{20} = +25° \pm 1.5°$ (c=1% in methylene chloride).

EXAMPLE 15

2-amino-N-[(20S) 5α-pregnane-20-ol-3α-yl]-N-methyl-acetamide hydrochloride

The product of Example 14 was reduced to obtain (20S) 3α-methylamino-5α-pregnane-20-ol melting at 170° C. [described by Vetter et al, Bull. Soc., 1963, p. 1324] and the latter was reacted with BOC-glycine by the variant of Example 2 to obtain 2-amino-N-[(20S) 5α-pregnane-20-ol-3α-yl]-N-methyl-acetamide hydrochloride melting at ≃250° C.

EXAMPLE 16

2(S) 2-amino-N-methyl-N-[(20S) 5α-pregnane-20-ol-3α-yl]-propanamide hydrochloride Using the procedure of Example 1, BOC-glycine and (20S) 3α-methylamino-5α-pregnane-20-ol were reacted to obtain 2(S) 2-amino-N-methyl-N-[(20S) 5α-pregnane-20-1-3α-yl]-propanamide hydrochloride melting at >270° C.

EXAMPLE 17

2(R) 2-amino-N-methyl-N-[(20S) 5α-pregnane-20-ol-3α-yl]-propanamide hydrochloride Using the procedure of Example 2, BOC-Δ-alanine and (20S) 3α-methylamino-5α-pregnane-20-ol were reacted to obtain 2(R) 2-amino-N-methyl-N-[(20S) 5α-pregnane-20-ol-3α-yl]-propanamide hydrochloride which sublimated about 260° C.

EXAMPLE 18

(20S) 3α-ethylamino-5α-pregnane-20-ol-hydrochloride

Ethyl iodide and (20S) 3α-amino-5α-pregnane-20-ol were reacted in the presence of sodium carbonate to obtain (20S) 3α-ethylamino-5α-pregnane-20-ol melting at 129° C. after crystallization from ethyl acetate. An ethyl acetate solution saturated with hydrogen chloride was added to the said compound until an acid pH was reacted to obtain (20S) 3α-ethyl-amino-5α-pregnane-20-ol hydrochloride melting at >270° C.

EXAMPLE 19

2-amino-N-ethyl-N-[(20) 5α-pregnane-20-ol-3α-yl]-acetamide hydrochloride

The free base of Example 17 and BOC-L-glycine were reacted by the process of Example 2 to obtain 2-amino-N-ethyl-N-[(20) 5α-pregnane-20-ol-3α-yl]-acetamide hydrochloride melting at δ230° C.

EXAMPLE 20

(20S) 3α-[(2-hydroxyethyl)-amino]-5α-pregnane-20-ol-hydrochloride

A stirred suspension of 7 g of (20S) 3α-amino-5α-pregnane-20-ol and 7 g of sodium carbonate in 100 ml of anhydrous dioxane was refluxed for 24 hours under an inert atmosphere with 6.6 ml of 2-[2-bromoethoxy]-tetrahydrofuran and was then cooled to room temperature. The mixture was diluted with water and was extracted with ether. The organic phase was dried over magnesium sulfate, filtered and evaporated to dryness under reduced pressure. The residue was chromatographed over silica gel and was eluted with a 85-5-10 chloroform-methanol-acetic acid mixture to obtain 7.7 g of a yellow oil.

3 g of the oil were dissolved in 30 ml of ethanol and 15 ml of 2 N hydrochloric acid and the mixture was refluxed with stirring for 90 minutes and was then cooled and poured into 100 ml of aqueous sodium bicarbonate solution. The mixture was iced for 15 minutes and was then vacuum filtered. The product was washed with water, dried at 40° C. under reduced pressure and dissolved in 300 ml of methylene chloride containing 10% of methanol. The mixture was filtered and the filtrate was concentrated to obtain 50 ml and 10 ml of ethyl acetate were added. The mixture was evaporated to half its volume and was vacuum filtered. The product was dissolved in 100 ml of methanol and the solution was filtered. The filtrate was concentrated to 30 ml and 70 ml of ethyl acetate were added thereto. The volume was reduced by half and the mixture was vacuum filtered. The recovered product was dried at 40° C. under reduced pressure to obtain 1.65 g of (20S) 3α-[(2-hydroxyethyl)-amino]-5α-pregnane-20-ol melting at 215° C. 1.5 g of the latter were dissolved in 40 ml of methanol and a 1.6 N hydrogen chloride in ethyl acetate was added until the pH was acidic. 60 ml of ethyl acetate were added thereto and the mixture was concentrated under reduced pressure and was vacuum filtered. The product was dried at 40° C. under reduced pressure to obtain 1.5 g of (20S) 3α-[(2-hydroxyethyl)-amino]-5α-pregnane-20-ol hydrochloride melting at >270° C.

EXAMPLE 21

Tablets were prepared containing 10 mg of the product of Example 1 or 20 mg of 2-amino-N-[(20S) 5α-pregnane-20-ol-3α-yl]-propanamide hydrochloride or 15 mg of 2-amino-N-[(20S) 5α-pregnane-20-ol-3α-yl]-N-methyl-acetamide hydrochloride and sufficient excipient of talc, starch and magnesium stearate to obtain a final tablet of 100 mg.

PHARMACOLOGICAL DATA

The compound of Example 1 in the form of its hydrochloride (Product A) was compared with Levamisole, a product described in Vol. 9, Merck Index as No. 8949, which is known to possess immuno-regulating properties [Cancer Research, Vol. 35 (1975), p. 927 and New England Journal of Medicine Vol. 289, 21 (1973), p. 1148].

A. Potentialization of IgE production

Female mice weighing between 28 to 30 g were immunized by subcutaneous administration of an ovalbumin-alumina mixture on days 0 and 14 and serum was taken on the 21st day for dosage of IgE antibodies formed. The respective quantities of antigen (ovalbumin) and adjuvant (alumina) injected was selected so as to keep production of antibodies at a minimum. The test compounds were administered subcutaneously 3 hours before the first immunization.

The dosage of IgE effected using a passive cutaneous anaphylaxia test consisting of provoking in the animal by intraveinous administration of antigen an antigen-antibody reaction at a cutaneous site, where previous injection of antibodies prepared in another animal with the same antigen has been made. This reaction is usually increased by injection of a colorant at the same time as the antigen and the appearance at the point of injection of antibodies of a colored spot, is the control of the bursting of sensitized cells and of the resulting increase in capillary permeability. The research of the larger dilution of serum which gives a spot of a 11 to 13 mm diameter for each animal is made. An adequate dilution of serum was injected intradermally with a volume of 0.1 ml in male rats weighing about 250 g in the region of the back. 48 hours later, the animals received veinously 0.5 ml of a solution of 0.5% of ovalbumin and 1% of Evans blue in an isotonic solution of sodium chloride. 30 minutes after this injection, the animals were killed by exsanguination and the diameter of the blue spot on turned over skin is measured. The results obtained were 0.5 mg/kg for product A and 20 mg/kg for Levamisole, both administered subcutaneously. This means that product A in this test showed greater immunostimulating activity than Levamisole.

B. Adjuvant for chronic arthritis

The injection of a Freund type adjuvant (Mycobacterium butyricum at 6 mg/ml in Bayol 55) into the posterium paw of a rat provokes a primary inflammatory lesion and then after a latency period of 13 to 15 days, initiation of secondary inflammation affecting the other non-injected rear paw as well as the front paws, the ears and the tail. This secondary arthritis is comparable to human rheumatoid arthritis because the intervention of autoimmunitory reactions among other determining factors is admitted.

Male rats aged 42 to 50 days received an intraplantary injection of 0.10 ml of Freund adjuvant and treatment started the day of the adjuvant injection and continued until the animals were killed on the 17th day. The determining criteria of the activity of the substances were generally: increased weight of the animals which is always restrained proportionally to the intensity of the arthritis; increase in volume of the injected and non-injected rear paws in relation to the average volume of corresponding paws of control animals; arthritis of the front paws, of which the too small volume can not be measured by plethysmometry and thus a subjective scale of 0 to 3 following the intensity of the inflammation is established; arthritis of the ears and tail noted as 1 or 0 depending on the presence or absence of nodosities. In this test, the effect on secondary inflammations was essentially observed, it was determined by the arthritis of the non-injected rear paw, arthritis of the front paws and the inflammation of the ears and tail. The active dose which diminished the secondary inflammation by at least 50% was determined to be 1 mg/kg (subcutaneously) for product A and 50 mg/kg (orally) for Levamisole. This means product A is very active against secondary phenomena of arthritis of adjuvant as compared to a very high subtoxic dose of Levamisole to obtain a comparable effect.

C. Adjuvant for anaphylactic shock

The administration to animals of a compound capable of stimulating the activity of immunitary systems leads to an increase in response to administration of antigen to which the animal is sensitive. Male mice weighing between 30 to 35 g were sensitized by intraplantary administration of beef seric albumin. 8 days later, the mice received intraveinously an antigen and under the minimum sensibilization conditions, the control animals were not in mortal shock at the time of the last administration.

The test compound was injected intraplantary admixed with an antigen and if the product was an adjuvant, it increased the sensibilization and resulted in mortal shock with an intraveinous admnistration. The active dose which provoked a mortality equal to or greater than 50% of the animals was determined and the results are reported in Table I.

TABLE I

| Example No. | Dose in mg per animal |
|---|---|
| 2 | 0.5 |
| 3 | ≦1 |
| 5 | 5 |
| 6 | 5 |
| 7 | 2 |
| 8 | 1 |
| 9 | 5 |
| 10 | 1 |
| 11 | 0.5 |
| 14 | 5 |
| 15 | 0.5 |

D. Test of Rosettes to sheep red corpuscles

The administration to animals of a product capable of stimulating the immunitary systems leads to an increase of their capacity of reaction to the injection of an immunogenic product. 3 month old male rats were sensibilized by intraperitoneal administration of sheep erythrocytoes on day 0 and 7 days later, the spleen was removed and splenocytes were placed in contact with sheep erythrocytes. The percentage of leucocytes around the erythrocytes in the form of rosettes was determined. The test compounds were orally administered daily from day-1 to day 1 and immunostimulating dose is the dose of product which multiplied by 2 the percentage of rosettes observed in the control animals and the results are reported in Table II.

TABLE II

| Example No. | Dose in mg/kg |
|---|---|
| 2 | 1 |
| 6 | 2 |
| 7 | >5 |
| 9 | 5 |
| 11 | 5 |
| 12 | 5 |
| 15 | 10 |

E. Acute toxicity

The acute toxicity was determined as the lethal dose LD0 by orally administering the test compounds to mice and the maximum dose which did not cause any mortality after 8 days was determined. The results are reported in Table III.

TABLE III

| Example No. | DL0 in mg/kg |
|---|---|
| 2 | 200 |
| 3 | ≧400 |
| 4 | ≧400 |
| 5 | ≧400 |
| 6 | ≧1000 |
| 7 | ≧800 |
| 8 | ≧400 |
| 10 | ≧600 |
| 11 | ≧400 |
| 12 | ≧1000 |
| 13 | ≧400 |
| 14 | ≧400 |
| 15 | ≧200 |

Various modifications of the compounds and process of the invention may be made without departing from the spirit or scope thereof and it is to be understood that the invention is intended to be limited only as defined in the appended claims.

What we claim:

1. A compound selected from the group consisting of 3-amino-steroids of the formula

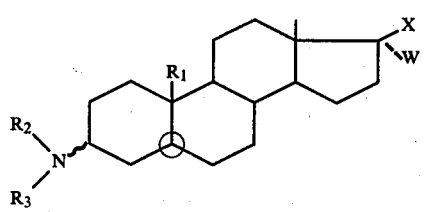

wherein W is selected from the group consisting of hydrogen and —OH, X is

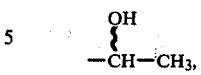

the wavy line indicates the substituent has the α- or β-position, $R_1$ is selected from the group consisting of hydrogen and —CH$_3$, $R_2$ is selected from the group consisting of hydrogen and alkyl of 1 to 5 carbon atoms, $R_3$ is selected from the group consisting of hydrogen, alkyl of 1 to 5 carbon atoms, hydroxy-alkyl of 2 to 5 carbon atoms, acyl of an organic acid of 2 to 8 carbon atoms, alkoxycarbonyl of 2 to 8 carbon atoms, acyl of an α-amino carboxylic acid and a peptide of 2 to 3 α-amino-carboxylic acids and their non-toxic, pharmaceutically acceptable acid addition salts with the proviso that $R_2$ and $R_3$ are not both hydrogen and (i) when $R_1$ is methyl, $R_2$ and W are hydrogen, X is

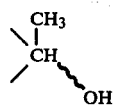

with the —OH having the (S) configuration and the amino group is in the α-position in the case $R_3$ is not methyl (ii) $R_2$ and W are hydrogen, X is

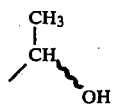

and the 3-amino is in the α-position in the case at least one of $R_1$, $R_2$ and $R_3$ is not methyl and (iii) $R_2$ and W are hydrogen, $R_1$ is methyl, X is

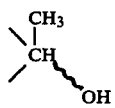

with the —OH having the (R) configuration and the 3-amino-in the α-position in the case $R_3$ is not ethoxycarbonyl.

2. A compound of claim 1 wherein $R_2$ is hydrogen or methyl.

3. A compound of claim 1 selected from the group consisting of (20S) 3α-[aminoacetylamino]-5α-pregnane-20-ol, 2-amino-N-[(20S) 5α-pregnane-20-ol-3α-yl]-1H-indol-3-propanamide, 2-amino-N-[(20S) 5α-pregnane-20-ol-3α-yl]-1H-3-propanamide, 2-amino-N-[(20S) 19-nor-5α-pregnane-20-ol-3α-yl]-acetamide, 2-amino-N-[(20S) 5α-pregnane-20-ol-3α-yl]-N-methyl-acetamide and their non-toxic, pharmaceutically acceptable acid addition salts.

4. A composition for the treatment of autoimmuno maladies comprising an effective amount of at least one compound of claim 1 and an inert pharmaceutical carrier.

5. A composition of claim 4 wherein $R_2$ is hydrogen or methyl.

6. A composition of claim 4 wherein the active compound is selected from the group consisting of (20S) 3α-[aminoacetylamino]-5α-pregnane-20-ol, 2-amino-N-

[(20S) 5α-pregnane-20-ol-3α-yl]-propanamide, (2S) 2-amino-N-[(20S) 5α-pregnane-20-ol-3α-yl]-1H-indol-3-propanamide, 2-amino-N-[(20S) 19-nor-5α-pregnane-20-ol-3α-yl]-acetamide, 2-amino-N-[(20S) 5α-pregnane-20-ol-3α-yl]-N-methyl-acetamide and their non-toxic, pharmaceutically acceptable acid addition salts.

7. A method of treating autoimmuno maladies in warm-blooded animals comprising administering to warm-blooded animals an amount of at least one compound of claim 1 sufficient to treat autoimmuno maladies.

8. The method of claim 7 wherein the compound is in the hydrochloride form.

9. A method of claim 7 wherein $R_2$ is hydrogen or methyl.

10. A method of claim 7 wherein the active compound is selected from the group consisting of (20S) 3α-[amino-acetylamino]-5α-pregnane-20-ol, 2-amino-N-[(20S) 5α-pregnane-20-ol-3α-yl]-propanamide, (2S) 2-amino-N-[(20S) 5α-pregnane-20-ol-3α-yl]-1H-indol-3-propanamide, 2-amino-N-[(20S) 19-nor-5α-pregnane-20-ol-3α-yl]-acetamide, 2-amino-N-[(20S) 5α-pregnane-20-ol-3α-yl]-N-methyl-acetamide and their non-toxic, pharmaceutically acceptable acid addition salts.

* * * * *